United States Patent
Sakai et al.

(10) Patent No.: US 9,766,115 B2
(45) Date of Patent: Sep. 19, 2017

(54) BALANCE ABILITY MEASUREMENT APPARATUS, BALANCE ABILITY MEASUREMENT METHOD AND NON-TRANSITORY COMPUTER READABLE RECORDING MEDIUM FOR RECORDING BALANCE ABILITY MEASUREMENT PROGRAM

(71) Applicant: Tanita Corporation, Tokyo (JP)

(72) Inventors: Yoshio Sakai, Tokyo (JP); Tomoko Takehara, Tokyo (JP)

(73) Assignee: Tanita Corporation, Tokyo (JP)

( * ) Notice: Subject to any disclaimer, the term of this patent is extended or adjusted under 35 U.S.C. 154(b) by 91 days.

(21) Appl. No.: 14/849,706

(22) Filed: Sep. 10, 2015

(65) Prior Publication Data

US 2016/0076930 A1 Mar. 17, 2016

(30) Foreign Application Priority Data

Sep. 12, 2014 (JP) .................................. 2014-186600

(51) Int. Cl.
*G01G 19/50* (2006.01)
*A61B 5/103* (2006.01)
(Continued)

(52) U.S. Cl.
CPC ........... *G01G 19/44* (2013.01); *A61B 5/1036* (2013.01); *A61B 5/4023* (2013.01); *G01G 19/50* (2013.01)

(58) Field of Classification Search
CPC ...... G01G 19/44; G01G 19/50; A61B 5/1036; A61B 5/4023
See application file for complete search history.

(56) References Cited

U.S. PATENT DOCUMENTS

| 2,374,105 A | * | 4/1945 | Kraus | .................... G01G 19/44 73/172 |
| 2,653,475 A | * | 9/1953 | Kraus | .................... G01G 19/44 177/200 |

(Continued)

FOREIGN PATENT DOCUMENTS

JP 4925284 B2 4/2012

OTHER PUBLICATIONS

Extended European Search Report issued in corresponding European Patent Application No. 15181532.1 dated Jan. 26, 2016.

*Primary Examiner* — Randy Gibson
(74) *Attorney, Agent, or Firm* — Morgan, Lewis & Bockius LLP (57) ABSTRACT

A balance ability measurement apparatus acquires load information on weight of a user as measured during a period of a stand-up movement which is a period of time from when the user starts the stand-up movement to when the user stabilizes standing posture. Based on the load information, the balance ability measurement apparatus calculates load change information on change in the weight of the user. Further, based on the load information, the balance ability measurement apparatus calculates left-right displacement information on displacement of the user in left-right direction. Based on the load change information and the left-right displacement information, the balance ability measurement apparatus calculates a balance ability evaluation value on balance ability of the user.

8 Claims, 6 Drawing Sheets

(51) Int. Cl.
*G01G 19/44* (2006.01)
*A61B 5/00* (2006.01)

(56) References Cited

U.S. PATENT DOCUMENTS

| | | | | |
|---|---|---|---|---|
| 3,616,690 A * | 11/1971 | Harden | ........... | G01G 3/08 |
| | | | | 177/200 |
| 4,014,398 A * | 3/1977 | Gresko | ........... | A61B 5/1036 |
| | | | | 177/208 |
| 5,337,757 A * | 8/1994 | Jain | ........... | G01G 19/44 |
| | | | | 434/258 |
| 6,360,597 B1 * | 3/2002 | Hubbard, Jr. | ........... | A43B 3/00 |
| | | | | 73/172 |
| 6,402,635 B1 * | 6/2002 | Nesbit | ........... | A63B 69/3667 |
| | | | | 473/131 |
| 6,437,257 B1 * | 8/2002 | Yoshida | ........... | A61B 5/1036 |
| | | | | 177/199 |
| 7,100,439 B2 * | 9/2006 | Carlucci | ........... | G01G 19/44 |
| | | | | 177/199 |
| 7,127,376 B2 * | 10/2006 | Nashner | ........... | A61B 5/1036 |
| | | | | 702/185 |
| 2004/0118617 A1 * | 6/2004 | Carlucci | ........... | G01G 19/44 |
| | | | | 177/25.11 |
| 2004/0127337 A1 | 7/2004 | Nashner | | |
| 2004/0163855 A1 * | 8/2004 | Carlucci | ........... | G01G 19/44 |
| | | | | 177/200 |
| 2005/0075833 A1 * | 4/2005 | Nashner | ........... | A61B 5/1036 |
| | | | | 702/179 |
| 2007/0093989 A1 * | 4/2007 | Nashner | ........... | A61B 5/1036 |
| | | | | 702/185 |
| 2011/0251520 A1 * | 10/2011 | Shieh | ........... | A43B 3/0005 |
| | | | | 600/587 |
| 2014/0180172 A1 | 6/2014 | Uchiyama | | |
| 2014/0200733 A1 * | 7/2014 | Sunaoshi | ........... | A61B 5/743 |
| | | | | 700/302 |
| 2014/0272853 A1 * | 9/2014 | Sakai | ........... | A61B 5/1036 |
| | | | | 434/247 |

* cited by examiner

FIG. 7

BALANCE ABILITY MEASUREMENT APPARATUS, BALANCE ABILITY MEASUREMENT METHOD AND NON-TRANSITORY COMPUTER READABLE RECORDING MEDIUM FOR RECORDING BALANCE ABILITY MEASUREMENT PROGRAM

CROSS-REFERENCE TO RELATED APPLICATION

This application is based on and claims the benefit of priority of the prior Japanese Patent Application No. 2014-186600, filed on Sep. 12, 2014, the entire contents of which are incorporated herein by reference.

BACKGROUND OF THE INVENTION

1. Field of the Invention

The present invention relates to a balance ability measurement apparatus, a balance ability measurement method and a non-transitory computer readable recording medium for recording a balance ability measurement program.

2. Description of the Related Art

A conventional method for evaluating balance ability uses a stabilometer to measure total trajectory length, trajectory length per unit time and center of gravity sway parameters such as center of gravity sway area, and evaluate the balance ability from the measurement results. For example, Japanese Patent Publication No. 4925284 discloses a technology to measure motor function of a subject or user by changing the standing posture of the subject and calculating center of gravity sway parameters. Another method for evaluating balance ability uses physical performance tests such as a one-leg standing test with open eyes, a one-leg standing test with closed eyes, an FR (Functional Reach) test, a TUG (Time Up and Go) test and so on. Still another method for evaluating balance ability uses Berg Balance Scale (BBS).

However, the method for evaluating balance ability of a subject, using a stabilometer to make measurements, has problems that measurement time increases, and that differences in measured values are less likely to occur among healthy subjects and subjects in secondary prevention or so, making it difficult to evaluate balance ability with high accuracy. Further, the method for evaluating balance ability using physical performance tests has inherent problems that measurement time increases, and that the reliability and objectivity of the evaluation value is not necessarily high. In addition, the method for evaluating balance ability using Berg Balance Scale has an inherent problem that the method cannot be carried out in the absence of an expert such as a physical therapist, an occupational therapist or the like.

BRIEF SUMMARY OF THE INVENTION

An object of the present invention is to provide a balance ability measurement apparatus, a balance ability measurement method, and a non-transitory computer readable recording medium for recording a balance ability measurement program which can measure balance ability with high accuracy.

According to a first aspect of the present invention, this object is achieved by a balance ability measurement apparatus comprising: acquisition circuitry configured to acquire load information on weight of a user as measured during a period of a stand-up movement which is a period of time from when the user starts the stand-up movement to when the user stabilizes standing posture; load change information calculation circuitry configured to calculate, based on the load information, load change information on change in the weight of the user; left-right displacement information calculation circuitry configured to calculate, based on the load information, left-right displacement information on displacement of the user in left-right direction; and balance ability evaluation value calculation circuitry configured to calculate, based on the load change information and the left-right displacement information, a balance ability evaluation value on balance ability of the user.

According to a second aspect of the present invention, the above object is achieved by a balance ability measurement method comprising the steps of: acquiring load information on weight of a user as measured during a period of a stand-up movement which is a period of time from when the user starts the stand-up movement to when the user stabilizes standing posture; calculating, based on the load information, load change information on change in the weight of the user; calculating, based on the load information, left-right displacement information on displacement of the user in left-right direction; and calculating, based on the load change information and the left-right displacement information, a balance ability evaluation value on balance ability of the user.

According to a third aspect of the present invention, the above object is achieved by a non-transitory computer readable recording medium for recording a balance ability measurement program to cause a computer to perform a process comprising the steps of: acquiring load information on weight of a user as measured during a period of a stand-up movement which is a period of time from when the user starts the stand-up movement to when the user stabilizes standing posture; calculating, based on the load information, load change information on change in the weight of the user; calculating, based on the load information, left-right displacement information on displacement of the user in left-right direction; and calculating, based on the load change information and the left-right displacement information, a balance ability evaluation value on balance ability of the user.

While the novel features of the present invention are set forth in the appended claims, the present invention will be better understood from the following detailed description taken in conjunction with the drawings.

BRIEF DESCRIPTION OF THE DRAWINGS

The present invention will be described hereinafter with reference to the annexed drawings. It is to be noted that the drawings are shown for the purpose of illustrating the technical concepts of the present invention or embodiments thereof, wherein:

FIG. 4B is a schematic view showing a state in which the user starts a stand-up movement from the chair, while

DETAILED DESCRIPTION OF THE INVENTION

Exemplary embodiments of the present invention will be described hereinafter with reference to the drawings. It is to be understood that the embodiments described herein are not intended as limiting, or encompassing the entire scope of, the present invention.

Figure 1:
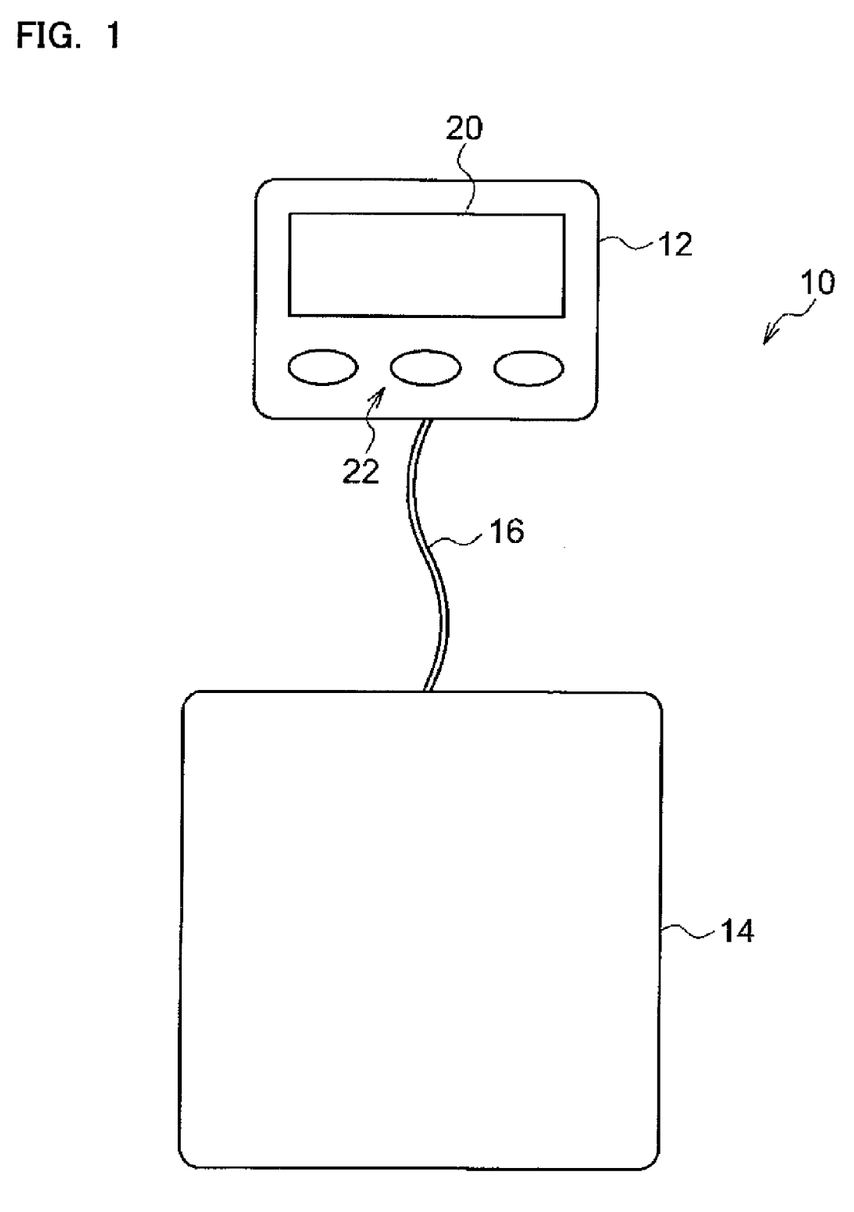
FIG. 1 is a schematic view showing the appearance of a balance ability measurement apparatus according to an exemplary embodiment of the present invention.
Figure 2:
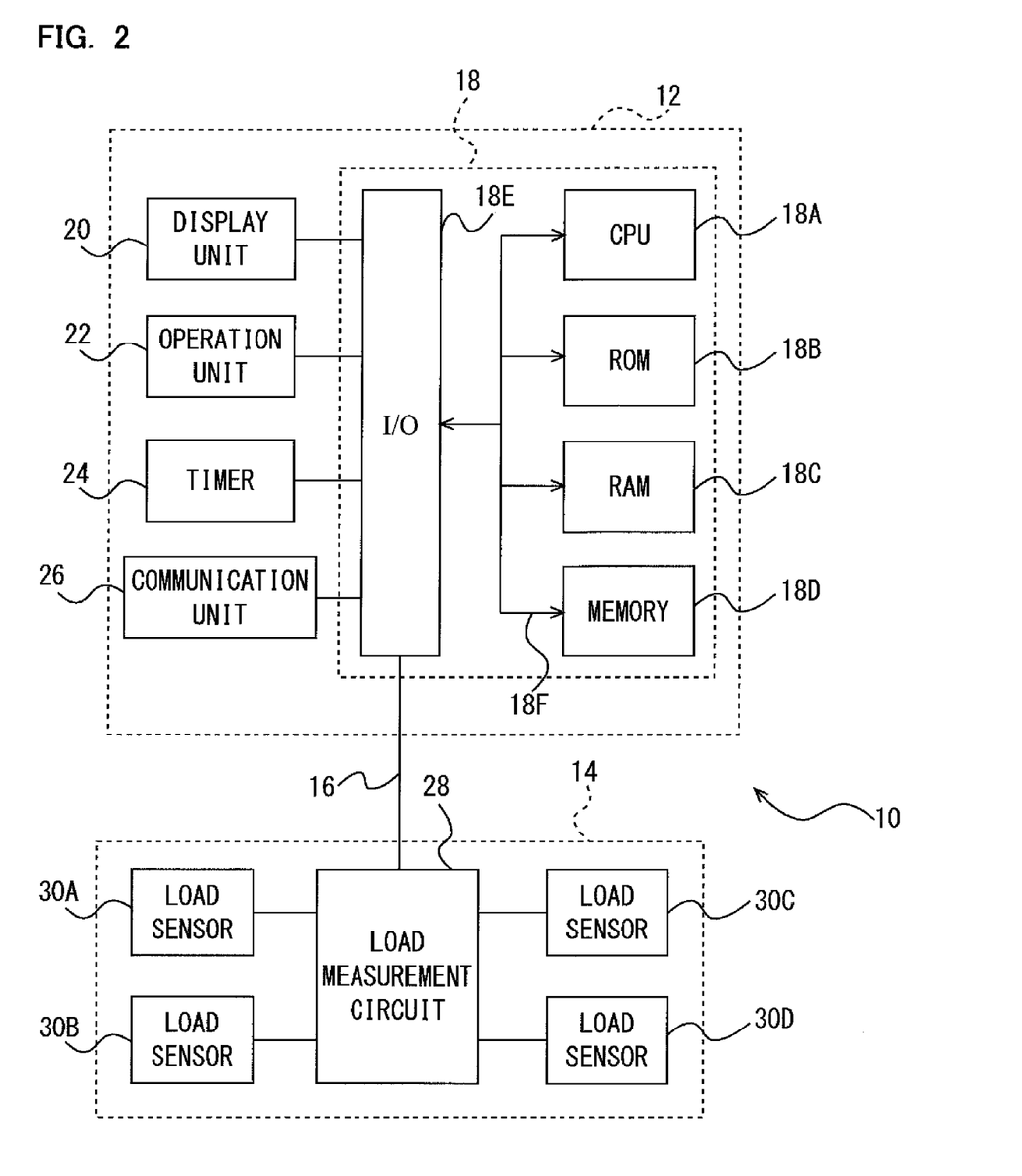
FIG. 2 is a schematic block diagram of the balance ability measurement apparatus.

FIG. 1 is a schematic view showing the appearance of a balance ability measurement apparatus 10 according to an exemplary embodiment of the present invention. As shown in FIG. 1, the balance ability measurement apparatus 10 comprises a display device 12 and a measurement table 14. The display device 12 and the measurement table 14 are connected to each other by a communication cable 16. FIG. 2 is a schematic block diagram of the balance ability measurement apparatus 10. The display device 12 comprises a controller 18, a display unit 20, an operation unit 22, a timer 24 and a communication unit 26.

The controller 18 comprises a CPU (Central Processing Unit) 18A, a ROM (Read Only Memory) 18B, a RAM (Random Access Memory) 18C, a memory 18D and an input/output interface (I/O) 18E which are connected to one another by a buss 18F. In this case, a balance ability measurement program to cause the CPU 18A of the controller 18 (or computer) to perform a balance ability measurement process as described later is written or recorded, for example, in the memory 18D, and is read in and executed by the CPU 18A. Thus, it can be said that the memory 18D is a non-transitory computer readable recording medium for recording the balance ability measurement program to cause the computer to perform the balance ability measurement process. Note that the balance ability measurement program can be provided by another recording medium such as a CD-ROM, a memory card or the like, or can be downloaded from a server (not shown).

The display unit 20, the operation unit 22, the timer 24 and the communication unit 26 are connected to the I/O 18E. The display unit 20 comprises, for example, a liquid crystal panel or the like. The display unit 20 displays various screens such as various setting screens, a screen showing a measurement result of the balance ability evaluation value of a user (subject) which is measured with the measurement table 14, and the like. As shown in FIG. 1, the operation unit 22 includes multiple operation buttons, and is used by the user to instruct the CPU 18A to perform various operations such as turning on/off power supply, inputting user information, and the like. Note that the display unit 20 and the operation unit 22 can be formed as a touch panel with a screen which is directly touched to perform various operations.

The timer 24 has a function to acquire the current time, and a function to measure time. The communication unit 26 sends and receives information to and from an external device via wireless or wired communication. This makes it possible for the balance ability measurement apparatus 10 to communicate with mobile devices such as a cellular phone, a smart phone, a tablet terminal and the like, and with external devices such as a personal computer and the like. The measurement table 14 comprises, for example, a load measurement circuit 28 and four load sensors 30A to 30D composed of two load sensors arranged in the left-right direction and two load sensors arranged in the front-back direction as described later. The load measurement circuit 28 is connected to the display device 12 by the communication cable 16.

Each of the load sensors 30A to 30D comprises, for example, a load cell to measure or detect load (weight of the user). In the following, a data representing a load measured by each of the load sensors 30A to 30D will be referred to as unit load data, while the total load obtained by summing the loads measured or detected by the respective load sensors 30A to 30D, that is, a data representing the weight of the user will be referred to as total load data. When instructed by the controller 18 to make measurements, the load measurement circuit 28 sends load information (information on the weight of the user) to the controller 18 at a predetermined sampling interval t, in which the load information includes the unit load data measured by the load sensors 30A to 30D, and the total load data obtained by summing the unit load data measured by the load sensors 30A to 30D. Note that the sampling interval t is, for example, 12.5 ms or so, but is not limited thereto.

Figure 3:
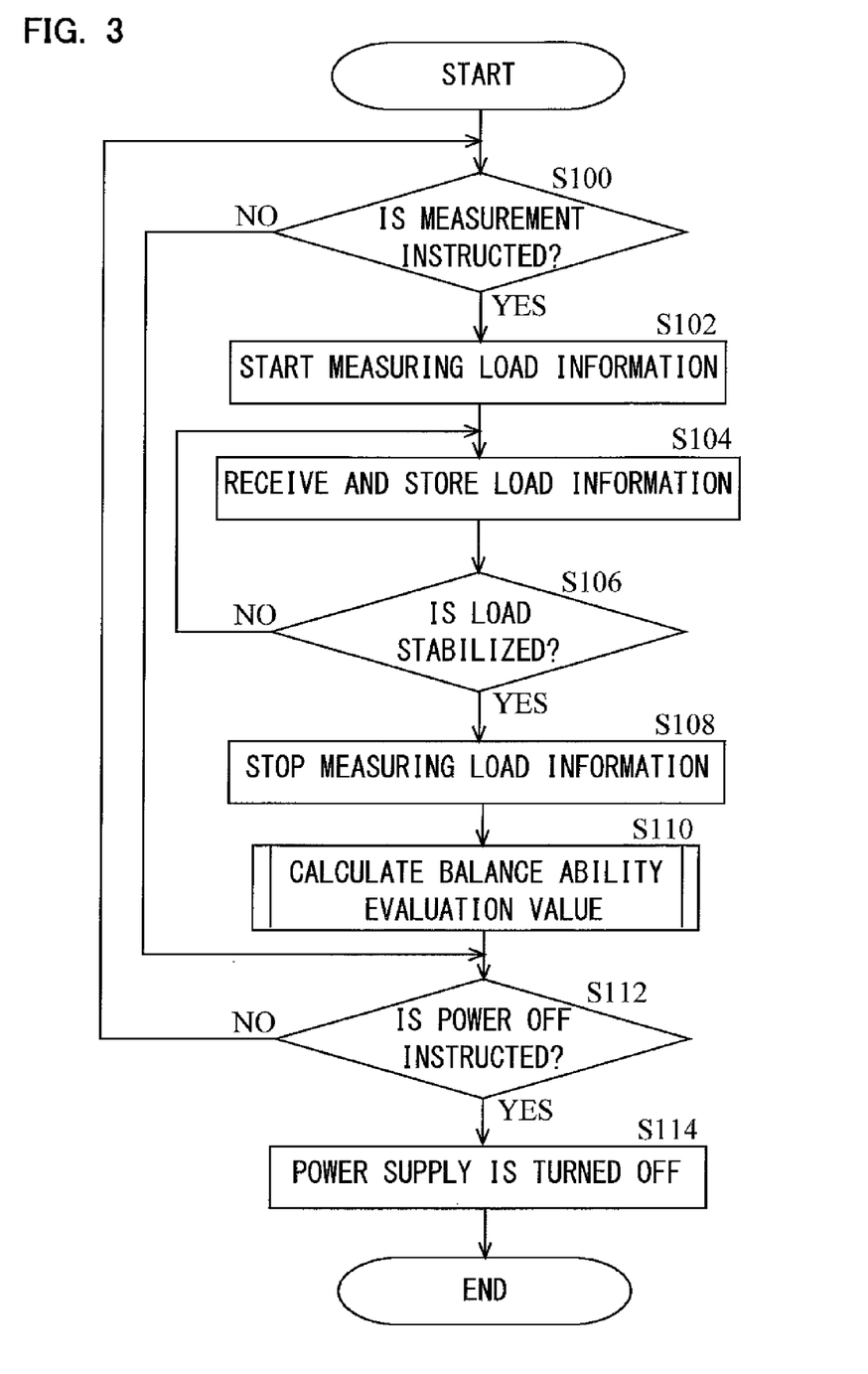
FIG. 3 is a flow chart of a process to be performed by a balance ability measurement program.

Next, referring to the flow chart shown in FIG. 3, a balance ability measurement process, which is performed by a balance ability measurement program to be executed by the CPU 18A of the controller 18 as an effect of the present embodiment, will be described. The process shown in FIG. 3 is performed when a power supply (not shown) of the balance ability measurement apparatus 10 is turned on. First, in step S100, the CPU 18A determines whether or not a user 32 (refer to FIGS. 4A to 4C) has operated the operation unit 22 of the display device 12 to instruct the CPU 18A to measure balance ability of the user 32. If the balance ability measurement has been instructed, the flow goes to step S102, while if the balance ability measurement has not been instructed, the flow goes to step S112.

Figure 4A:
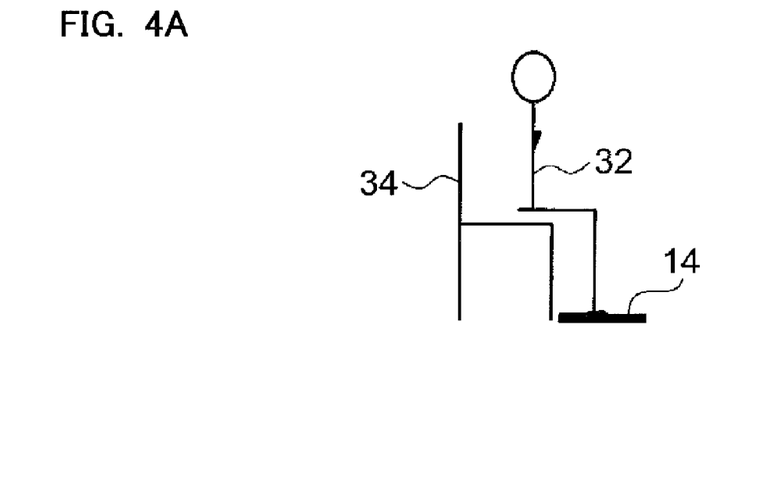
FIG. 4A is a schematic view showing a state in which a user (subject) sits on a chair.
Figure 4B:
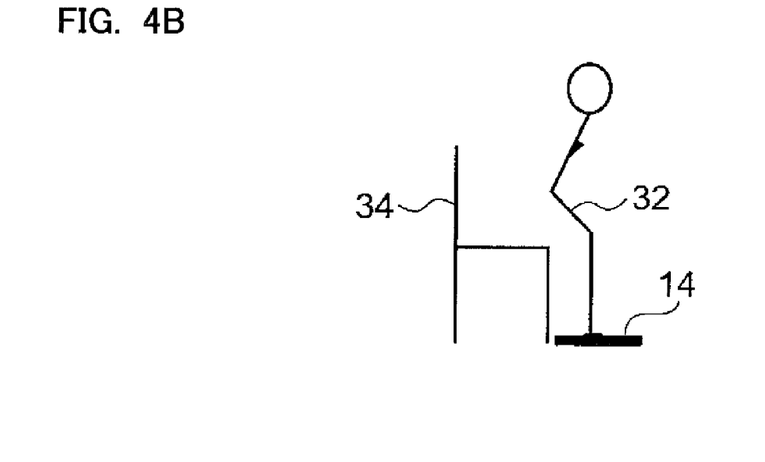
Figure 4C:
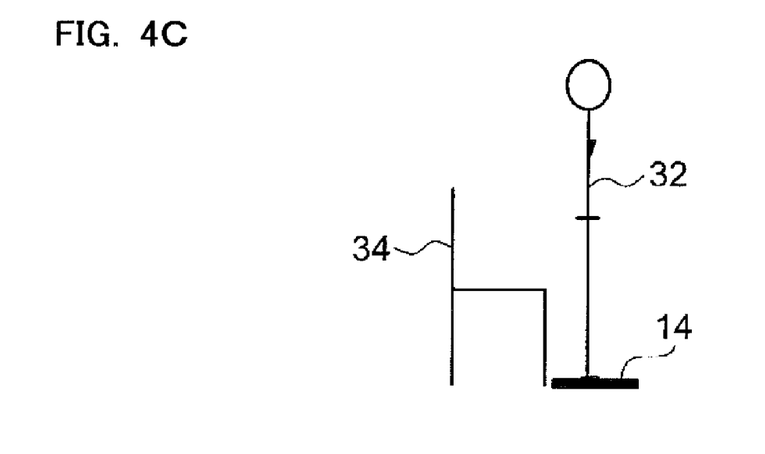
FIG. 4C is a schematic view showing a state in which the user stabilizes standing posture after fully standing up from the chair (or from sitting posture)

In step S102, the CPU 18A starts measuring or acquiring load information on the user. First, the CPU 18A measures the zero point which is an output of the load measurement circuit 28 when the user 32 is not on the measurement table 14, that is, an output in a no-load state. Thereafter, the CPU 18A causes the display unit 20 to display an indication that the load information measurement can be started. For example, the CPU 18A causes the display unit 20 to display "0.0 kg". Then, as shown in FIG. 4A, the user 32 sits on a chair 34 with both feet on the measurement table 14. The balance ability measurement apparatus 10 measures load information during a period of a stand-up movement which is a period of time from when the user 32 starts the stand-up movement (from the chair 34 or from sitting posture) to when the user 32 stabilizes standing posture (after fully standing up) as shown in FIGS. 4A to 4C. Thus, the CPU 18A (with its associated components of the balance ability measurement apparatus 10) functions as acquisition circuitry configured to measure or acquire the load information on the weight of the user as measured during the period of the stand-up movement. Based on the measured load information, the balance ability measurement apparatus 10 calculates the balance ability evaluation value on the balance ability of the user 32.

Next, the CPU 18A instructs the load measurement circuit 28 to start measuring load information. Thus, the load measurement circuit 28 sends the load information, which includes the unit load data measured by the load sensors 30A to 30D and the total load data obtained by summing the unit load data measured by the load sensors 30A to 30D, to the controller 18 at a predetermined sampling interval t. In step S104, the controller 18 receives the load information sent from the load measurement circuit 28, and the CPU 18A associates the load information with the current time acquired by the timer 24, and stores the load information associated with the current time in the memory 18D. In step S106, the CPU 18A determines whether or not the load has been stabilized. If the load has been stabilized, the flow goes to step S108, while if the load has not been stabilized, the flow returns to step S104.

The determination of whether or not the load has been stabilized is made, for example, by determining whether or not a fluctuation in the load falls within a predetermined range. The determination of whether or not the load has been stabilized can also be made, for example, by calculating a standard deviation or dispersion indicating change in the total load data measured during a predetermined period of time from a point in the past to the present, and by determining whether or not the standard deviation or dispersion thus calculated is equal to or lower than a predetermined threshold value. In step S108, the CPU 18A instructs the load measurement circuit 38 to stop measuring the load information. Thus, the load measurement circuit 28 stops measuring the load information, and stops sending the load information to the controller 18.

Figure 5:
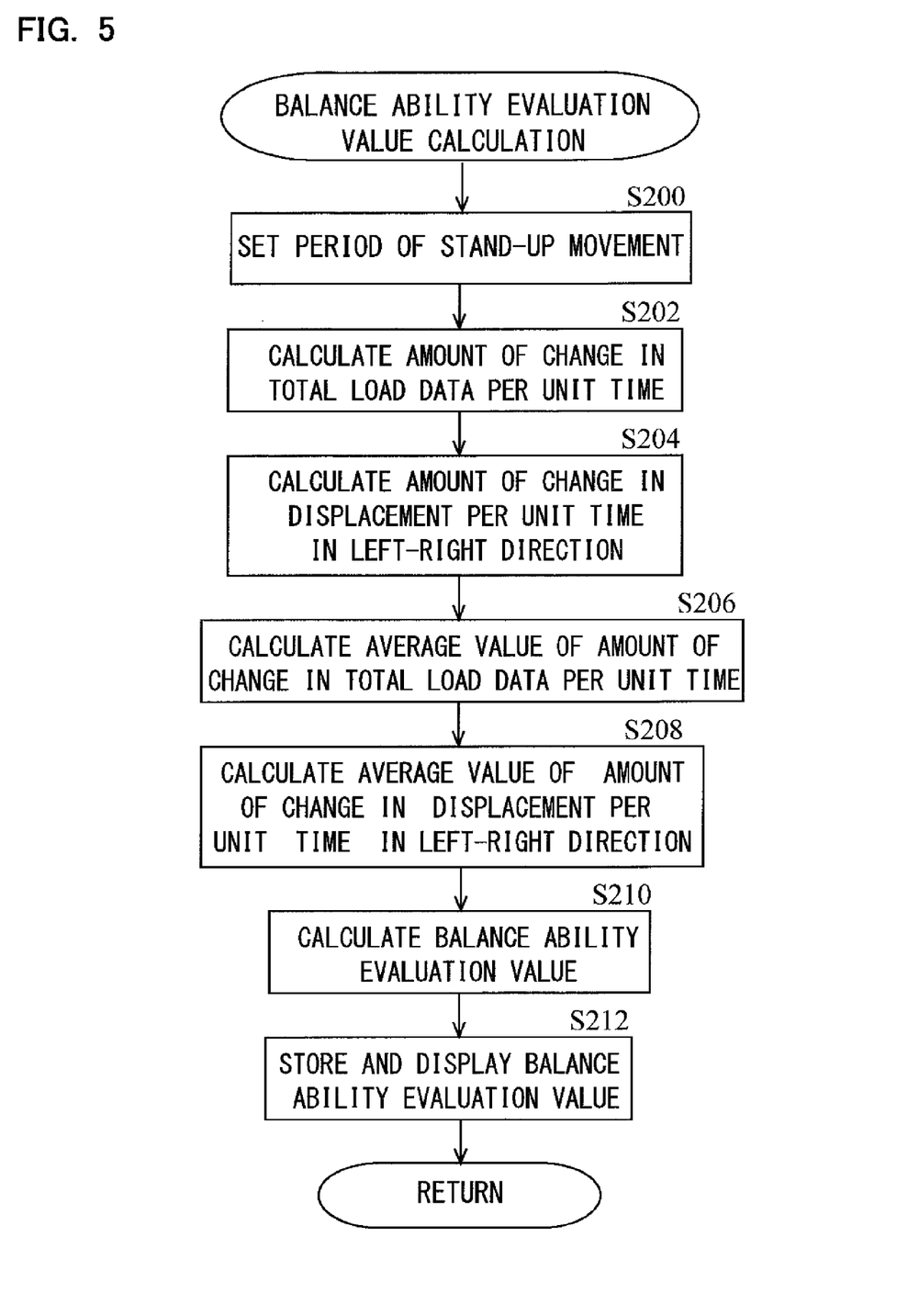
FIG. 5 is a flow chart of a routine to calculate a balance ability evaluation value.
Figure 6:
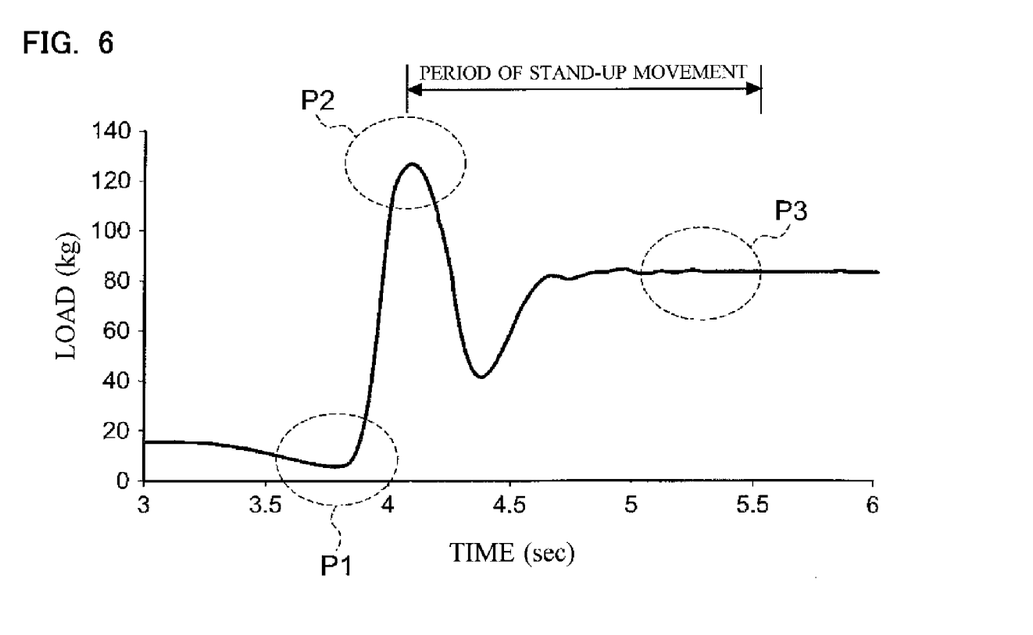
FIG. 6 is a graph showing an example of total load data.

In step S110, the CPU 18A performs a process to calculate the balance ability evaluation value as shown in FIG. 5. In step S112, the CPU 18A determines whether or not the user has instructed the CPU 18A to turn off the power supply (not shown). If the user has instructed to turn off the power supply, the flow goes to step S114, while if the user has not instructed to turn off the power supply, the flow returns to step S100 to perform the same process as described above. In step S114, the power supply is turned off to end the routine. In step S200 in FIG. 5, the CPU 18A sets a period of the stand-up movement based on the measured total load data. FIG. 6 is a graph showing an example of total load data measured on a user with a weight of about 80 kg. The load (kg) on the vertical axis is the value of the sum of the unit load data measured by the four load sensors 30A to 30D.

Referring to FIG. 6, a point P1 indicated by a dashed circle is a point when the user 32 is about to start the stand-up movement in a state where the user 32 sits on the chair 34 as shown in FIG. 4A, and is a point when the load is momentarily reduced. On the other hand, a point P2 indicated by a dashed circle in FIG. 6 is a point when the hips of the user 32 have just lifted off the chair 34 as shown in FIG. 4B, and is a point when a maximum value of the load is applied to the measurement table 14. Further, a point P3 indicated by a dashed circle in FIG. 6 is a point when the user 32 has stood up from the chair 34 and stabilized its standing posture, and thus the load has been stabilized as shown in FIG. 4C. The load measured at the point P3 is the weight of the user 32. In the present embodiment, the period from the point P2 to the point P3, for example, is set as the period of the stand-up movement. However, the period from the point P1 to the point P3 can also be set as the period of the stand-up movement.

In step S200, the CPU 18A refers to the total load data stored in the memory 18D to determine the point P2 when the maximum value of the load is applied, and the point P3 when the load is stabilized. More specifically, the point P2 can be determined, for example, by detecting a point corresponding to a maximum value of total load data among the measured total load data. Further, the point P3 can be determined, for example, by calculating a standard deviation or dispersion of the total load data for each predetermined period for the total load data measured after the point P2, and by detecting a point when the calculated standard deviation or dispersion first becomes equal to or lower than a predetermined threshold value. Thus, the period from the point P2 to the point P3 is set as the period of the stand-up movement. In the case of setting the period from the point P1 to the point P3 as the period of the stand-up movement, the point P1 can be determined, for example, by detecting a point corresponding to a minimum value of total load data among the measured total load data.

In step S202, the CPU 18A calculates an amount of change in the total load data per unit time as load change information indicating (or load change information on) change in the weight of the user. More specifically, assuming that $W_1, W_2, \ldots W_{n-1}$ (kg) are n number of total load data measured at a sampling interval t during the period of the stand-up movement, and $vW_1, vW_2, \ldots vW_{n-1}$ (kg/sec) are the amount of change in the total load data per unit time, the CPU 18A calculates $vW_1=(W_2-W_1)/t$, $vW_2=(W_3-W_2)/t$, ... $vW_{n-1}=(W_n-W_{n-1})/t$. Thus, the CPU 18A (with its associated components of the balance ability measurement apparatus 10) functions as load change information calculation circuitry configured to calculate, based on the load information, the load change information on the change in the weight of the user.

Figure 7:
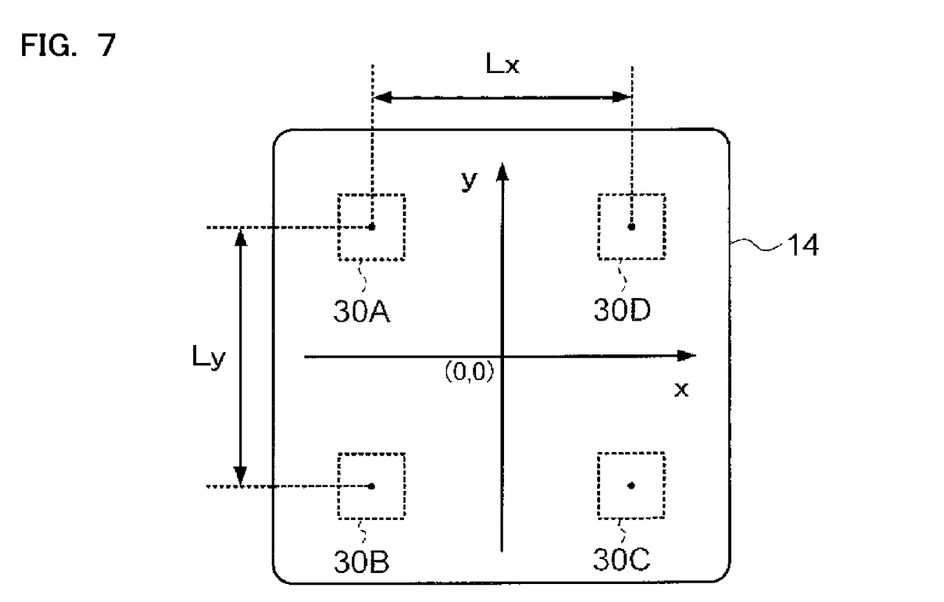
FIG. 7 is a chart for explaining the calculation of displacement in left-right direction.

In step S204, the CPU 18A calculates an amount of change in displacement of the user per unit time in left-right direction as left-right displacement information (that is, information on displacement of the user in the left-right direction). More specifically, based on unit load data measured by the load sensors 30A to 30D at n sampling points in the period of the stand-up movement, the CPU 18A calculates a displacement of the user in the left-right direction for each of the n sampling points. Even more specifically, the calculation will be made below. Note that the present embodiment describes a case where the load sensors 30A to 30D are equidistantly arranged in each of the X-axis and Y-axis directions on the measurement table 14 as shown in FIG. 7. Further, in the present embodiment, the X-axis and Y-axis directions are assumed as left-right and front-back directions, respectively. In other words, it is assumed that the user 32 places both feet on the measurement table 14 such that the line connecting the toe and heel of each foot is oriented in the Y-axis direction, so as to measure the balance ability evaluation value.

Assuming that Lx (mm) is a distance between the load sensor 30A (load sensor 30B) and the load sensor 30C (load sensor 30D) in the X-axis direction, Ly (mm) is a distance between the load sensor 30A (load sensor 30C) and the load sensor 30B (load sensor 30D) in the Y-axis direction, while $WA_i$, $WB_i$, $WC_i$, $WD_i$ are unit load data measured by the load sensors 30A to 30D, respectively, the CPU 18A calculates a displacement $DX_i$ (i =1, 2, . . . n) (of the center of the load) in the left-right direction at each of the n sampling points in the period of the stand-up movement by the following equation (1). Note that as shown in FIG. 7, the intersection point of the X-axis and the Y-axis, which is the origin (0, 0), is the center of the load sensors 30A to 30D.

$$DX_i = Lx \times (-WA_i - WB_i + WC_i + WD_i)/W_i \quad (1)$$

Here, $W_i$ is the total load data indicating the total load obtained by summing the unit load data $WA_i$, $WB_i$, $WC_i$, $WD_i$. Assuming that $vDX_1, vDX_2, \ldots vDX_n$ (mm/sec) are the amount of change in the displacement of the user (i.e. the center of the load) per unit time in left-right direction at the n sampling points, respectively, the CPU 18A calculates $vDX_1=(DX_2-DX_1)/t$, $vDX_2=(DX_3-DX_2)/t$, ... $vDX_{n-1}=$ $(DX_n - DX_{n-1})/t$. Thus, the CPU 18A (with its associated components of the balance ability measurement apparatus 10) functions as left-right displacement information calculation circuitry configured to calculate, based on the load information, the left-right displacement information on the displacement of the user in left-right direction.

In step S206, the CPU 18A uses the following equation (2) to calculate an average value vWav of the amount of change in the total load data per unit time, which is calculated in step S202, as a representative value of the amount of change in the total load data per unit time.

$$vWav = (|vW_1| + |vW_2| + \ldots + |vW_{n-1}|)/(n-1) \quad (2)$$

Note that the representative value of the amount of change in the total load data per unit time is not limited to the average value, but can be, for example, a weighted average value, a central value, a standard deviation, dispersion, or the like.

In step S208, the CPU 18A uses the following equation (3) to calculate an average value vDXav of the amount of change in the displacement per unit time in the left-right direction, which is calculated in step S204, as a representative value of the amount of change in the displacement per unit time in the left-right direction.

$$vDXav = (|vDX_1| + |vDX_2| + \ldots + |DX_{n-1}|)/(n-1) \quad (3)$$

Note that the representative value of the amount of change in the displacement per unit time in the left-right direction is not limited to the average value, but can be, for example, a weighted average value, a central value, a standard deviation, dispersion, or the like.

In step S210, the CPU 18A uses the following equation (4) to calculate a balance ability evaluation value B based on the average value vWav of the amount of change in the total load data per unit time as calculated in step S206 and the average value vDXav of the amount of change in the displacement per unit time in the left-right direction as calculated in step S208.

$$B = vDXav/vWav \quad (4)$$

Thus, in the present embodiment, the value obtained by dividing the average value vDXav of the amount of change in the displacement per unit time in the left-right direction by the average value vWav of the amount of change in the total load data per unit time is used as the balance ability evaluation value B. Thus, the CPU 18A (with its associated components of the balance ability measurement apparatus 10) functions as balance ability evaluation value calculation circuitry configured to calculate, based on the load change information and the left-right displacement information, the balance ability evaluation value on the balance ability of the user.

If the average value vDXav of the amount of change in the displacement per unit time in the left-right direction is high, the user is presumed to be standing up while swaying left and right or leaning to one side. If the average value vDXav of the amount of change in the displacement per unit time in the left-right direction is low, the user is presumed to be moving little left and right and standing up straight. On the other hand, if the average value vWav of the amount of change in the total load data per unit time is high, the user is presumed to be standing up strongly and quickly. If the average value vWav of the amount of change in the total load data per unit time is low, the user is presumed to be standing up slowly. Thus, it can be said that as the balance ability evaluation value B increases, the balance of the user is worse.

If the balance ability is assumed to be evaluated by only the average value vDXav of the amount of change in the displacement per unit time in the left-right direction, the average value vDXav would be relatively high also when the user stands up quickly. This is because, as shown in the above equation (1), the displacement $DX_i$ in the left-right direction is calculated based on the unit load data $WA_i$, $WB_i$, $WC_i$, $WD_i$, and therefore, if the user stands up quickly, the load would fluctuate significantly. Thus, in the case of a user with high balance ability, such as a member of an athletic club in a university, the use of only the average value vDXav of the amount of change in the displacement per unit time in the left-right direction to evaluate the balance ability causes the balance ability to be erroneously evaluated as low, even if the balance ability is high.

In contrast, in the present embodiment, the value obtained by dividing the average value vDXav of the amount of change in the displacement per unit time in the left-right direction by the average value vWav of the amount of change in the total load data per unit time is used as the balance ability evaluation value B. Since it can be said that the average value vWav of the amount of change in the total load data per unit time represents a fluctuation in the load in the vertical direction, the balance ability evaluation value can be calculated by removing the influence of the fluctuation in the load. Thus, the balance ability can be evaluated with high accuracy. Further, in the case of a user with low balance ability, such as an aged person requiring care, the average value vDXav of the amount of change in the displacement per unit time in the left-right direction is usually high, while the average value vWav of the amount of change in the total load data per unit time is usually low. This causes the balance ability evaluation value B to be quite high, and therefore, it is found reasonable to use the above equation (4) to calculate the balance ability evaluation value B.

As described above, in the present embodiment, the balance ability can be evaluated with high accuracy because the balance ability evaluation value B is calculated using both the average value vDXav of the amount of change in the displacement per unit time in the left-right direction, which represents a movement or sway of the user in the left-right direction, and the average value vWav of the amount of change in the total load data per unit time which represents a movement or sway of the user in the vertical direction. Further, the balance ability can be measured if there is a space to place the measurement table 14 and the chair 34, and the measurement can be made with just a daily activity of standing up, making it possible to easily measure the balance ability in a reduced space. Further, while a user with lower balance ability is more likely to fall down, the likelihood of falling down can be estimated by knowing the balance ability based on the balance ability evaluation value as calculated in the present embodiment. Furthermore, since the balance ability of the user is known based on the balance ability evaluation value as calculated in the present embodiment, the user can be efficiently trained according to the balance ability.

It is to be noted that the equation to calculate the balance ability evaluation value B is not limited to the above equation (4). For example, a term for an amount of change in displacement of the user (i.e. the center of the load) per unit time in front-back direction can be added to the equation (4) to calculate the balance ability evaluation value B. More specifically, the following equation (5) can be used to calculate the balance ability evaluation value B.

$$B=(vDXav/vWav) \times \alpha + vDYav \times \beta \quad (5)$$

Here, $\alpha$ and $\beta$ are predetermined coefficients which are determined, for example, based on measurement results of the balance ability evaluation values of many subjects. Note that while multiplication with $\alpha$ and $\beta$ is used in the equation (5), another operation such as addition can be used instead. In the equation (5), vDYav is an average value of an amount of change in the displacement of the user per unit time in the front-back direction, and is more specifically calculated as follows.

First, the CPU 18A uses the following equation (6) to calculate a displacement $DY_i$ (i=1, 2, ... n) (of the center of the load) in the front-back direction at each of the n sampling points in the period of the stand-up movement.

$$DY_i = Ly \times (WA_i - WB_i - WC_i + WD_i) / W_i \quad (6)$$

Next, assuming that $vDY_1, DY_2, \ldots vDY_N$ (mm/sec) are the amount of change in the displacement per unit time in front-back direction at the n sampling points, respectively, the CPU 18A calculates $vDY_1 = (DY_2 - DY_1 - DY_1)/t$, $vDY_2 = (DY_3 - DY_2)/t, \ldots vDY_{n-1} = (DY_n - DY_{n-1})/t$. Thereafter, the CPU 18A uses the following equation (7) to calculate an average value vDYav of the amount of change in the displacement per unit time in the front-back direction as a representative value of the amount of change in the displacement per unit time in the front-back direction.

$$vDYav = (|vDY_1| + |vDY_2| + \ldots + |DY_{n-1}|)/(n-1) \quad (7)$$

Thus, the CPU 18A (with its associated components of the balance ability measurement apparatus 10) functions as a front-back displacement information calculation circuitry configured to calculate, based on the unit load data, the representative value of the amount of change in the displacement of the user per unit time in the front-back direction during the period of the stand-up movement. Note that the representative value of the amount of change in the displacement per unit time in the front-back direction is not limited to the average value, but can be, for example, a weighted average value, a central value, a standard deviation, dispersion, or the like.

Here, when the user starts the stand-up movement in a state where the user sits on the chair 34, the center of gravity of the user moves forward. If the user has low balance ability, the user stands up while moving in the front-back direction, and therefore, the average value vDYav of the amount of change in the displacement per unit time in the front-back direction is high. On the other hand, if the user has high balance ability, the center of gravity of the user moves smoothly, and therefore, the average value vDYav of the amount of change in the displacement per unit time in the front-back direction is low.

Further, if the user has low muscle strength (typically such as an aged person or the like), the user may not be able to stand up with only the force of its legs, and thus may largely move its upper body and stand up using the momentum of this movement, which also causes a large movement in the front-back direction. If the user thus stands up by largely moving its upper body, it can be considered that the user has low muscle strength and difficulty in posture control, and therefore that the user has low balance ability. This means that, in either case, the user has low balance ability if the average value vDYav of the amount of change in the displacement per unit time in the front-back direction is high. Thus, the balance ability evaluation value can be measured with even higher accuracy if the average value vDYav of the amount of change in the displacement per unit time in the front-back direction is added to the equation (4) to calculate the balance ability evaluation value.

Furthermore, for example, a term for a period of a stand-up movement of the user can be added to the equation (4) to calculate the balance ability evaluation value B. More specifically, assuming that ST is a period of a stand-up movement, the CPU 18A uses the following equation (8) to calculate the balance ability evaluation value B.

$$B = (vDXav/vWav) \times \alpha + ST \times \gamma \quad (8)$$

Here, $\gamma$ is a predetermined coefficient which is determined, for example, based on measurement results of the balance ability evaluation values of many subjects. Note that while multiplication with $\gamma$ is used in the equation (8), another operation such as addition can be used instead. Further, the period ST of the stand-up movement can be calculated by subtracting the time at the point P2 from the time at the point P3 as shown in FIG. 6. Thus, the CPU 18A (with its associated components of the balance ability measurement apparatus 10) functions as a period calculation circuitry configured to calculate the period of the stand-up movement based on the load information.

The period ST of the stand-up movement is the time from when the user starts a stand-up movement from the chair 34 (or from its sitting posture) to when the user stabilizes its standing posture. If the period ST of the stand-up movement is long, it means that the user takes a long time from when the user starts the stand-up movement from the chair 34 to when the user stabilizes its standing posture, making it possible to say that the user has low balance ability. On the other hand, if the period ST of the stand-up movement is short, it means that the user quickly stabilizes its standing posture after the user starts the stand-up movement from the chair 34, making it possible to say that the user has high balance ability. Thus, the balance ability can be measured with even higher accuracy if the period ST of the stand-up movement is added to the equation (4) to calculate the balance ability evaluation value B as in the above equation (8).

In addition, both the term for the amount of change in displacement of the user per unit time in front-back direction and the term for the period ST of the stand-up movement of the user can be added to the equation (4) to calculate the balance ability evaluation value B. More specifically, the CPU 18A can use the following equation (9) to calculate the balance ability evaluation value B.

$$B = (vDXav/vWav) \times \alpha + vDYav \times \beta + ST \times \gamma \quad (9)$$

Note that while multiplication with $\alpha$, $\beta$ and $\gamma$ is used in the equation (9), another operation such as addition can be used instead.

Thus, the balance ability evaluation value can be measured with even higher accuracy if both the amount of change in the displacement of the user per unit time in the front-back direction and the period ST of the stand-up movement of the user are added to the equation (4) to calculate the balance ability evaluation value B. Note that it is possible to use, for example, user information including at least one of gender, age and body size (including, for example, at least one of height and weight) of the user 32 to weight the coefficients $\alpha$, $\beta$ and $\gamma$ in the above equations (5), (8) and (9). This makes it possible to measure the balance ability of the user with even higher accuracy.

As shown in FIG. 1, the display device 12 and the measurement table 14 of the balance ability measurement apparatus 10 in the present embodiment described above are separate from each other. However, the display device 12 and the measurement table 14 may be integral with each other. Further, the balance ability measurement apparatus 10 in the present embodiment described above comprises four load sensors composed of two load sensors arranged in the left-right direction and two load sensors arranged in the front-back direction, but is not limited thereto. If the balance ability measurement apparatus 10 (the CPU 18A) calculates balance ability evaluation values using only the amount of change in displacement of the user or subject per unit time in the left-right direction, it is sufficient that the balance ability measurement apparatus 10 comprises two load sensors arranged in the left-right direction. Further, if the balance ability measurement apparatus 10 calculates balance ability evaluation values using the amount of change in the displacement per unit time in front-back direction in addition to the amount of change in displacement per unit time in the left-right direction, it is sufficient that at least one load sensor in the front-back direction is added to provide at least three load sensors in total.

Furthermore, for example, a personal computer or the like, or a mobile terminal such as a cellular phone, a smart phone, a tablet terminal or the like can be used as the display device 12 of the balance ability measurement apparatus 10. In this case, the measurement table 14 is provided with a communication function to send load information from the measurement table 14 to the mobile terminal, the personal computer or the like. The mobile terminal, the personal computer or the like receives and acquires the load information sent from the measurement table 14, and executes the balance ability measurement program as shown in FIG. 3. Thus, the mobile terminal, the personal computer or the like can be allowed to function as the balance ability measurement apparatus.

It is to be noted that the present invention is not limited to the above-described embodiments and modified examples, and various modifications are possible within the spirit and scope of the present invention. The present invention has been described above using exemplary embodiments, but such description should not be interpreted as limiting the present invention. Various modifications will become obvious, evident or apparent to those ordinarily skilled in the art, who have read the description. Accordingly, the appended claims should be interpreted to cover all modifications and alterations which fall within the spirit and scope of the present invention.

The invention claimed is:

1. A balance ability measurement apparatus comprising:
acquisition circuitry configured to acquire unit load data measured by each of load sensors, and total load data obtained by summing the unit load data and representing weight of a user;
period setting circuitry configured to set, based on the total load data, a period of a stand-up movement which is a period of time from when the user starts the stand-up movement to when the user stabilizes standing posture;
load change information calculation circuitry configured to calculate, based on the total load data, a representative value of an amount of change in the total load data per unit time during the period of the stand-up movement;
left-right displacement information calculation circuitry configured to calculate, based on the unit load data, a representative value of an amount of change in the displacement of the user per unit time in left-right direction during the period of the stand-up movement; and
balance ability evaluation value calculation circuitry configured to calculate a balance ability evaluation value on balance ability of the user, based on the representative value of the amount of change in the total load data per unit time and the representative value of the amount of change in the displacement of the user per unit time in the left-right direction.

2. The balance ability measurement apparatus according to claim 1, further comprising
period calculation circuitry configured to calculate the period of the stand-up movement based on the total load data,
wherein the balance ability evaluation value calculation circuitry calculates the balance ability evaluation value based on:
the representative value of the amount of change in the total load data per unit time;
the representative value of the amount of change in the displacement of the user per unit time in the left-right direction; and
the period of the stand-up movement as calculated by the period calculation circuitry.

3. The balance ability measurement apparatus according to claim 2,
wherein the balance ability evaluation value calculation circuitry calculates the balance ability evaluation value by using user information including at least one of gender, age and body size to weight:
the representative value of the amount of change in the total load data per unit time;
the representative value of the amount of change in the displacement of the user per unit time in the left-right direction; and
the period of the stand-up movement as calculated by the period calculation circuitry.

4. The balance ability measurement apparatus according to claim 1, further comprising the load sensors,
wherein the load sensors are arranged in the left-right direction.

5. A balance ability measurement method comprising the steps of:
acquiring load information on weight of a user as measured during a period of a stand-up movement which is a period of time from when the user starts the stand-up movement to when the user stabilizes standing posture;
calculating, based on the load information, load change information on change in the weight of the user;
calculating, based on the load information, left-right displacement information on displacement of the user in left-right direction; and
calculating, based on the load change information and the left-right displacement information, a balance ability evaluation value on balance ability of the user.

6. A non-transitory computer readable recording medium for recording a balance ability measurement program to cause a computer to perform a process comprising the steps of:
acquiring unit load data measured by each of load sensors, and total load data obtained by summing the unit load data and representing weight of a user;
setting, based on the total load data, a period of a stand-up movement which is a period of time from when the user starts the stand-up movement to when the user stabilizes standing posture;

calculating, based on the total load data, a representative value of an amount of change in the total load data per unit time during the period of the stand-up movement;

calculating, based on the unit load data, a representative value of an amount of change in the displacement of the user per unit time in left-right direction during the period of the stand-up movement; and calculating a balance ability evaluation value on balance ability of the user, based on the representative value of the amount of change in the total load data per unit time and the representative value of the amount of change in the displacement of the user per unit time in the left-right direction.

7. The balance ability measurement apparatus according to claim 1, further comprising front-back displacement information calculation circuitry configured to calculate, based on the unit load data, a representative value of an amount of change in the displacement of the user per unit time in the front-back direction during the period of the stand-up movement, wherein the balance ability evaluation value calculation circuitry calculates the balance ability evaluation value based on:

the representative value of the amount of change in the total load data per unit time;

the representative value of the amount of change in the displacement of the user per unit time in the left-right direction; and the representative value of the amount of change in the displacement of the user per unit time in the front-back direction.

8. The balance ability measurement apparatus according to claim 7, wherein the balance ability evaluation value calculation circuitry calculates the balance ability evaluation value by using user information including at least one of gender, age and body size to weight:

the representative value of the amount of change in the total load data per unit time;

the representative value of the amount of change in the displacement of the user per unit time in the left-right direction; and the representative value of the amount of change in the displacement of the user per unit time in the front-back direction.

* * * * *